United States Patent
Butler et al.

(10) Patent No.: US 7,495,766 B2
(45) Date of Patent: Feb. 24, 2009

(54) SPECTROSCOPIC ANALYSIS TECHNIQUE FOR MEASURING THE AMOUNT OF SURFACE MATERIAL ON WIRE

(75) Inventors: Kevin Butler, Broadview Heights, OH (US); André J. Sommer, Oxford, OH (US)

(73) Assignee: Linccln Global, Inc., City of Industry, CA (US)

( * ) Notice: Subject to any disclaimer, the term of this patent is extended or adjusted under 35 U.S.C. 154(b) by 412 days.

(21) Appl. No.: 11/472,696

(22) Filed: Jun. 22, 2006

(65) Prior Publication Data

US 2007/0296975 A1   Dec. 27, 2007

(51) Int. Cl.
*G01N 21/84* (2006.01)
(52) U.S. Cl. ........................ 356/429; 356/430
(58) Field of Classification Search ................ 356/429, 356/430
See application file for complete search history.

(56) References Cited

U.S. PATENT DOCUMENTS

| | | | | |
|---|---|---|---|---|
| 4,358,202 | A * | 11/1982 | Puffer et al. ................. | 356/430 |
| 4,563,095 | A * | 1/1986 | Puffer ......................... | 356/430 |
| 5,162,131 | A * | 11/1992 | Rantanen et al. ............. | 427/10 |
| 5,225,661 | A | 7/1993 | Chai et al. | |
| 5,469,252 | A * | 11/1995 | Doles et al. ................ | 356/73.1 |
| 5,939,718 | A | 8/1999 | Yamada et al. | |
| 6,002,129 | A | 12/1999 | Ito et al. | |
| 6,041,096 | A | 3/2000 | Doi et al. | |
| 6,146,768 | A | 11/2000 | Masaie et al. | |
| 6,191,430 | B1 * | 2/2001 | Belotserkovsky et al. ..................... | 250/559.16 |
| 6,265,717 | B1 | 7/2001 | Sakata et al. | |
| 6,569,383 | B1 | 5/2003 | Nelson et al. | |
| 6,597,455 | B1 * | 7/2003 | Wlodarski et al. .......... | 356/430 |
| 6,708,877 | B2 | 3/2004 | Blankenship et al. | |
| 6,841,246 | B2 | 1/2005 | Shimizu et al. | |
| 6,882,701 | B2 | 4/2005 | Ferrandino et al. | |
| 6,887,713 | B2 | 5/2005 | Nelson et al. | |
| 6,906,285 | B2 | 6/2005 | Zucker et al. | |
| 6,937,691 | B2 | 8/2005 | Yamagami et al. | |
| 7,038,779 | B2 * | 5/2006 | Demarest et al. ............ | 356/430 |

(Continued)

FOREIGN PATENT DOCUMENTS

JP   60107564 A   11/1983

(Continued)

OTHER PUBLICATIONS

PerkinElmerSCIEX Instruments, "ICP Mass Spectrometry, The 30-Minute Guide to ICP-MS", 2001 PerkinElmer, Inc., 8 pgs.

*Primary Examiner*—Roy M Punnoose
(74) *Attorney, Agent, or Firm*—Fay Sharpe LLP

(57) ABSTRACT

In accordance with the present application, a method and system is provided for measuring an amount of surface material on a wire. A section of the wire and a beam generating device configured to generate a high energy beam are placed in a positional relationship with each other. The relationship permits a high energy beam generated from the beam generating device to impinge upon a location on the section of the wire. A reflected beam from the high energy beam is reflected from the section of the wire and is detected by a detector positioned at a location to receive the reflected beam. The beam received by the detector is investigated to determine the characteristics of the surface material on the wire.

20 Claims, 3 Drawing Sheets

U.S. PATENT DOCUMENTS

| | | |
|---|---|---|
| 7,307,729 B2 * | 12/2007 | Moshe ....................... 356/430 |
| 2004/0083958 A1 * | 5/2004 | Saidman et al. ............. 118/688 |
| 2005/0016976 A1 | 1/2005 | Belfiore et al. |
| 2005/0083005 A1 | 4/2005 | Enyedy et al. |
| 2005/0109936 A1 | 5/2005 | Yun et al. |
| 2006/0033919 A1 * | 2/2006 | Moshe ....................... 356/430 |

FOREIGN PATENT DOCUMENTS

| | | |
|---|---|---|
| JP | 09285864 A | 4/1996 |
| JP | 2000304742 A | 11/2000 |

* cited by examiner

SPECTROSCOPIC ANALYSIS TECHNIQUE FOR MEASURING THE AMOUNT OF SURFACE MATERIAL ON WIRE

BACKGROUND

The present application is directed to the measurement of material on the surface of an object, and more particularly, to the measuring of the amount of a substance on a wire, such as automatic welding wire.

To improve the welding process, the welding wire has a thin substance layer applied to its surface. The substance layer may be a lubricant such as oil. The amount of lubricant on the welding wire is known to have a direct impact on the overall welding process, and the amount and type can vary dependent on a variety of parameters including the type of wire, the type of welding process, as well as the material which is to be welded. The surface of the welding wire may also carry contaminants or residuals from the wire forming process. As shown in FIG. 1, uncoiled drawn welding wire 10, which has been drawn down to its final size, is passed through an applicator 12, which applies a layer of oil 14 or other lubricant to the outer surface of welding wire 10.

It has been noted above that lubrication of welding wire is beneficial in the welding process. In particular, oil or other lubricants provide at least two functions. In an automatic welding environment, the welding wire is automatically fed through a cable into a gun or torch. The cable may be of a significant length, therefore oil or other lubricant is used to lubricate the cable assembly as the wire is pushed through the cable to the gun or torch during the welding process. Additionally at times, stabilizers are used with the oil or lubricant for a smoother welding process.

To gain the benefit of the oil or lubricant application process, certain specifications need to be met. For example, an appropriate amount of oil or lubricant must be on the surface. Additionally, other specifications may permit only a certain amount of contaminants, or certain levels of additives or residual from the wire forming process. Testing is therefore undertaken to determine whether the oil, lubricant, additives, contaminants or residual material on the surface of the wire are within specifications determined to be desirable for a particular wire. Presently, the primary technique for performing the measurements, is by a crude weight loss technique. This technique can only be undertaken after the wire manufacturing process has been completed, and thus only provides results for a small fraction of the wire produced. The technique is also non-specific to the oil or lubricant, and is subject to errors resulting from sample preparation or the presence of other materials removed during the test.

Once the wire has been drawn and oiled, it is wound in large coils, such as coil 16 of FIG. 2, which may have thousands of feet of the drawn and oiled wire. The present testing process requires someone to unwind a portion of the coiled wire and either inspect a portion of the wire, including measuring the amount of oil on the surface, and/or taking a sample of the oil to thereafter measure characteristics of the oil such as the viscosity, oil composition, contaminants or other substances.

If this testing determines the oil is out of specification, additional wire is unwrapped from the coil and further testing is undertaken. In some situations, it may be necessary to unwrap the coil a number of times, peeling off 100 to 200 pounds of wire to perform these tests. This process goes on until the tested oil or lubricant is found to be within specification.

The foregoing testing procedure is cumbersome and tedious, as well as inefficient. Additionally, it is possible that during the application of the oil or other lubricant, the application process may go in and out of specification. Therefore, even if it is determined a portion of the wire is within specification, at a point further back on the coil the application process may have been out of specification, so there is no assurance the entire coil is within specification.

In consideration of the above, it is desirable to provide a method and system for measuring the amount of surface material on a wire, which permits for a faster, and more accurate measurement.

BRIEF DESCRIPTION

In accordance with the present application, a method and system is provided for measuring an amount of surface material on a wire. A section of the wire and a beam generating device configured to generate an electromagnetic light beam are placed in a positional relationship with each other. The relationship permits the light beam to impinge on a section of the wire. A reflected light beam from the incident beam is reflected from the section of the wire and is detected by a detector positioned at a location to receive the reflected light beam. The light beam received by the detector is investigated to determine the characteristics of the surface material on the wire. In one embodiment, the wire is moving and in another embodiment the wire is stationary.

DETAILED DESCRIPTION

Figure 1:
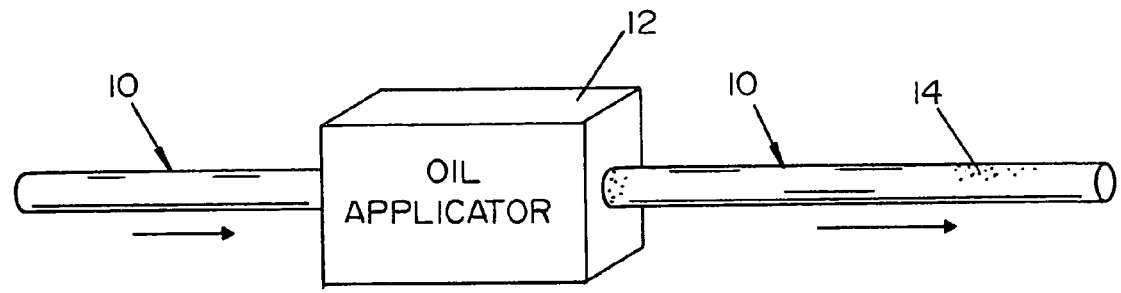
FIG. 1 is a block diagram illustrating an oil application process.
Figure 2:
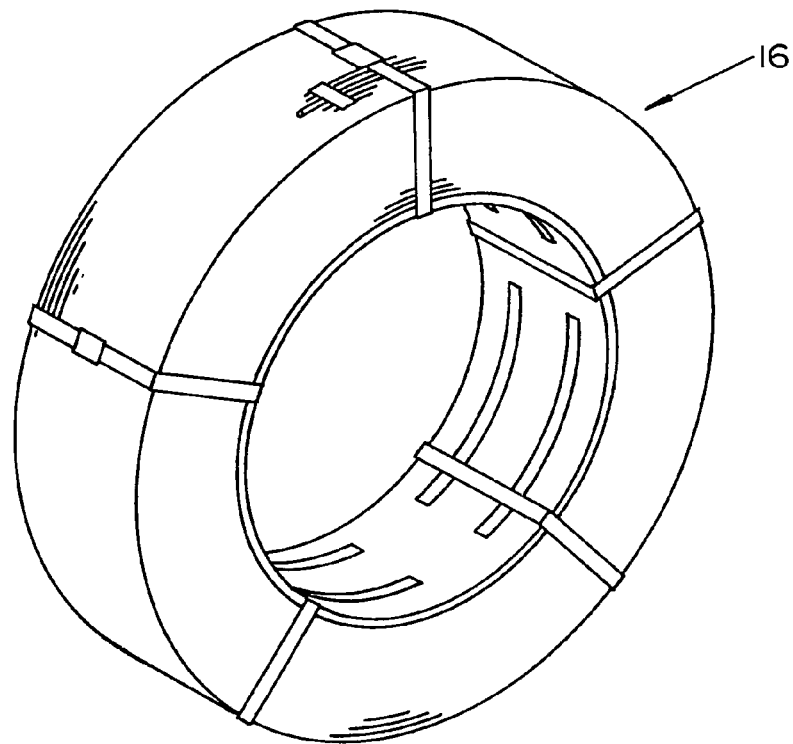
FIG. 2 illustrates a coil of oiled welding wire.
Figure 3:
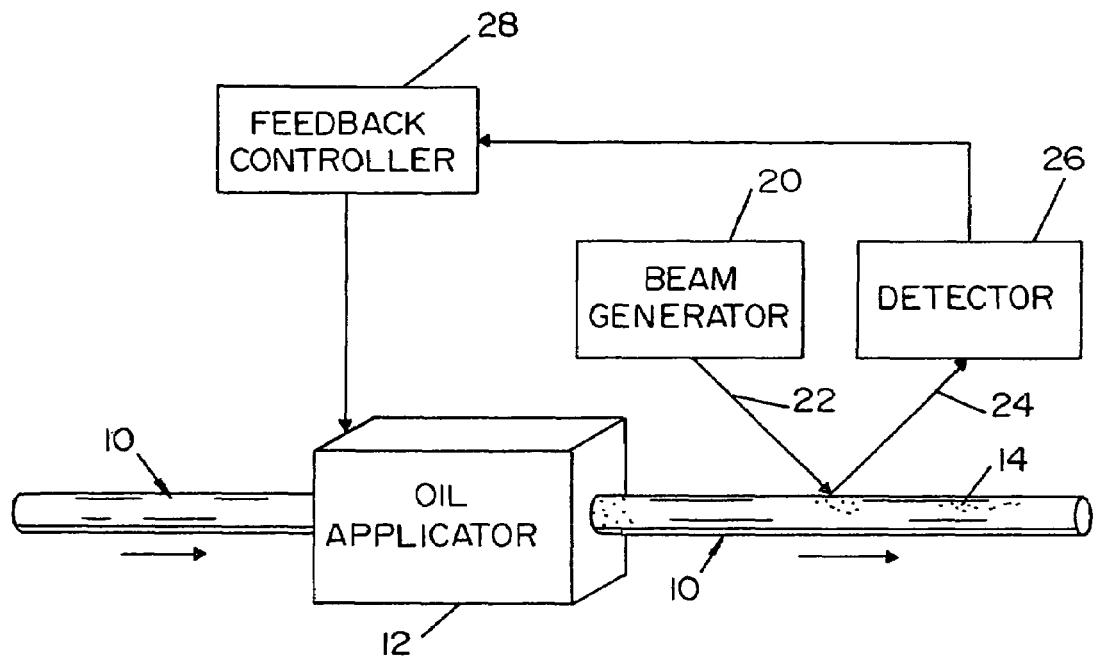
FIG. 3 depicts a detection system according to the present application where the wire is being tested in a real-time manner during the manufacturing process.

As depicted in FIG. 1, and similarly shown in FIG. 3, drawn wire 10 (in an uncoiled state) is passed through an applicator 12 which applies oil or other lubricant 14 to a surface of drawn wire 10. This oiled (or otherwise lubricated) and drawn wire (10, 14) is stored as coiled wire 16 as shown in FIG. 2. It is to be noted that while the following discussion focuses on a welding wire having a curved surface, the concepts may be applicable to other materials have different geometric configurations such as flat, concave or patterned among others.

In one embodiment, provided is a system and process, including a spectroscopic technique that measures the lubricant (e.g., oil) and/or contaminants on the surface of welding wire 10 as it is being manufactured. Thus, the technique shown in FIG. 3 provides for real-time measurement and testing of the oiled wire (10, 14). More particularly, an electromagnetic wave beam generator 20 is positioned in relationship to the oiled wire (10, 14) such that an emitted incident beam 22 impinges on a portion of the surface of oiled wire (10, 14) as it moves in the manufacturing process. Incident beam 22 is reflected or deflected from the surface of the oiled wire (10, 14) as deflected beam 24. A detector 26 is positioned in relationship to the oiled wire (10, 14) to receive the reflected/deflected beam 24. Due to the presence of certain organic molecules or functional groups in oil (or other lubricant) 14 on wire 10, a portion of the energy from the incident beam 22 is absorbed. Particularly, some of the organic compounds may absorb energy (i.e., specific wavelengths) of the incident beam 22 and thereby undergo certain transformations such as entering different vibrational states. Moving to these states causes absorption of certain amounts of energy. Therefore, the reflected beam 24 will have less energy than incident beam 22, and the reflected beam 24, detected by detector 26, is measured to determine the amount of lost energy occurring due to the vibrational changes in the organic compounds. The detection of lost energy is based on the wave length and/or energy of detected reflected beam 24 versus the wave length and/or energy of incident beam 22. By interpreting the detected beam, the identity and amount of material present on the surface of the oiled wire (10, 14) is determined, including the amount and characteristics of the oil (or lubricant) and/or contaminants such as residual drawing lubricants, as well as other impurities. The information obtained by the above process may be collected multiple times per second, as the oiled wire (10, 14) passes by detector 26.

Thus, the above arrangement permits real-time detection of organic materials present on the surface of welding wire. A particular advantage obtained by this process can be seen by the following example.

In the production of large runs of welding wire (e.g., 1000 lb. package), the amount of residual drawing lubricant and surface oil present on the wire is currently tested once the manufactured wire is formed as a coil. There is, therefore, an assumption the manufacturing control maintains the substances on the surface of the wire within certain limits or specifications while the manufacturing process is taking place. Thus, in the previous testing techniques, it was not possible, in a real-time, to detect if the application process moves out of specification.

However, as shown with further reference to FIG. 3, in the present embodiment the information obtained by detector 26 is provided to a feedback controller or circuit 28 which in turn feeds back control signals to applicator 12. Thus, during the manufacturing process when detector 26 begins to detect a movement of the oil and/or other materials outside of an acceptable range or specification, the data provided to feedback controller 28 is used to adjust the operation of applicator 12. For example, the rate at which oil is being applied to the surface may be increased or decreased as required, different mixtures of oil may be combined, or oils having different characteristics may be used by applicator 12. Thus, using the real-time information, the process is controlled to maintain the application process within specification.

With continuing attention to FIG. 3, while the foregoing discussion of FIG. 3 was directed to use of the testing system incorporating beam generator 20 and beam detector 26 within the actual manufacturing process, in an alternative embodiment, beam emitter 20 and detector 26 may be used when the oiled wire (10, 14) is stopped or offline. While stopping the manufacturing process before the coil package is complete is in some cases not desirable, if such a stoppage occurs, it can be used to test the surface of wire 14. When the manufacturing process does stop, testing will occur in a rapid fashion, as information using the above process can be collected multiple times per second. Then the collected data may be sent to feedback 28, for any corrective actions.

Figure 4:
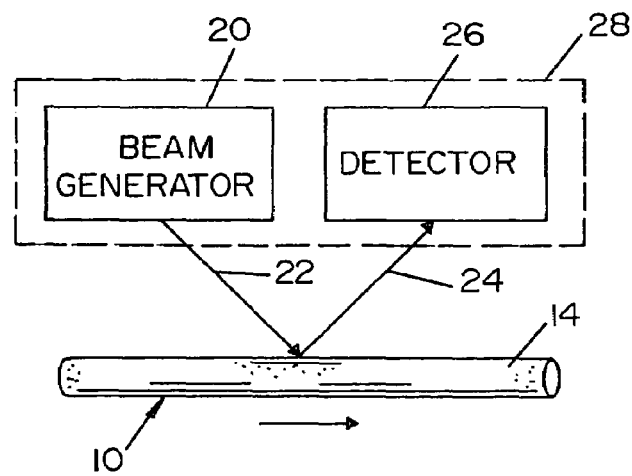
FIG. 4 depicts a testing of the wire in a static or offline manner.

In still a further embodiment, FIG. 4 permits for a situation where the manufacturing process has been completed and the oiled wire (10, 14) is in a coil 16 such as in FIG. 2. In this situation, offline testing may be undertaken using the beam generator 20, and detector 26. While this does not have the benefit of real-time analysis, and may require uncoiling of wire (if the wire has been coiled), the use of the high energy beam 22 and reflected beam 24 can provide quicker and more accurate analysis of the wire surface than other known techniques. In the offline embodiment, the beam generator 20 and detector 26 can be configured as a portable hand-held system 28.

Figure 5:
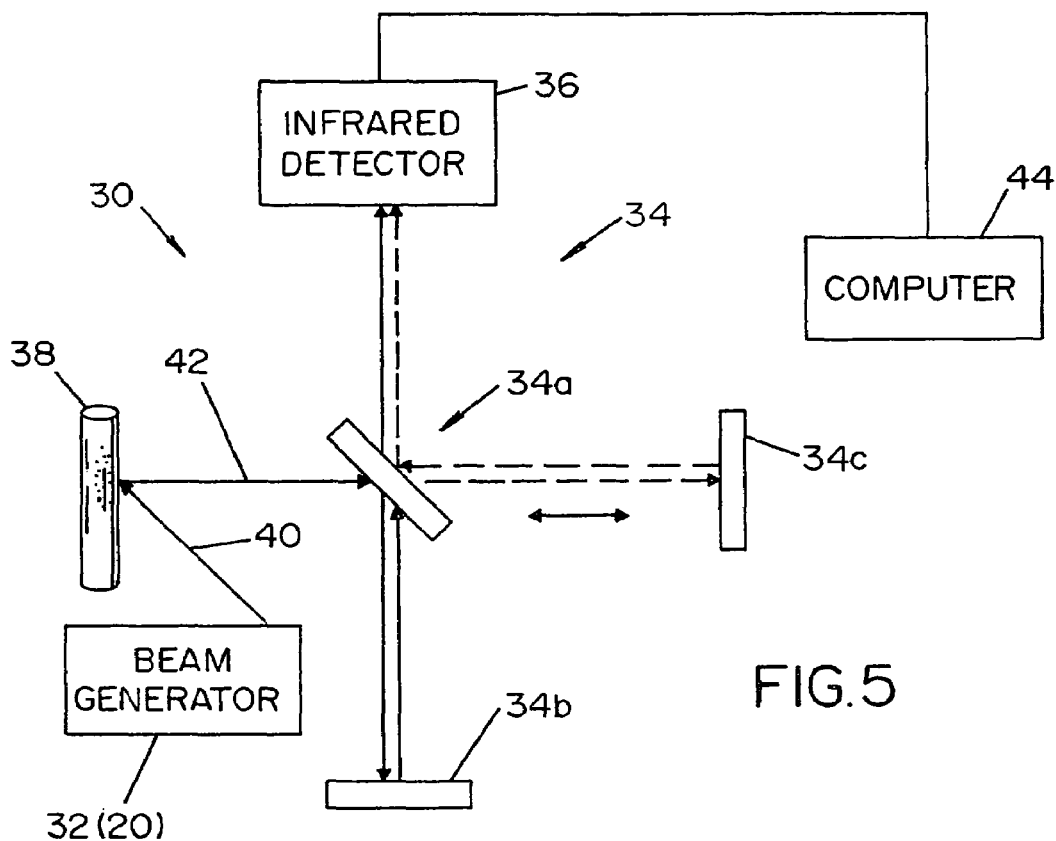
FIG. 5 illustrates one embodiment of a detection system which may be used in accordance with the present application; and, FIGS. 6A-6B depict an embodiment for stabilizing movement of the wire during the real-time investigation.

Also, beam generator 20 and detector 26 may be configured as a spectrographic analysis device. For example, as shown in FIG. 5, beam generator 20 and detector 26 may be implemented in the form of a Fourier-Transform Infrared (FTIR) spectrometer 30. A FTIR spectrometer consists in principle of an infrared source 32, as the beam generator of FIGS. 3 and 4; an interferometer 34; and an infrared detector 36, as the detector of FIGS. 3 and 4. The interferometer 34 consists in a simplified form as a beam splitter 34a, a fixed mirror 34b, and a moving mirror 34c, provided for scanning. By this design, sample 38 (e.g., oiled wire 10, 14), which has an incident infrared beam 40 impinged on its surface, and which is then reflected as reflected beam 42, is not directly measured but its interferogram, i.e., the IR intensity reaching the detector as a function of the mirror position provides the output data. The spectrum of the sample is subsequently obtained by Fourier transformations generated by operation of, for example, Fourier algorithm software running on computer 44, where the data from the interferogram is transposed from the time domain into the frequency domain.

As mentioned previously, the FTIR is useful in the above-described testing embodiments as it is able to perform multiple detections and data acquisition in a very short time period. This is beneficial for a manufacturing process which moves the wire at about 1000 ft/min or greater. Existing FTIR spectrometers have sufficiently fast data acquisition capabilities to capture the data generated at these speeds.

While FTIR is specifically recited as an instrument which could be used in connection with the described concepts, it is to be appreciated there are varieties of spectrometers now in use. Therefore, it is not intended that the present application be limited just to the use of FTIR techniques, but may be used with other data detection systems which permit or have the capability of detecting the characteristics of material on surface 10. Particularly, some oils or other materials may be detected at other light ranges such as in the visible light range and, therefore, analytical techniques such as elastic light scattering, and inelastic light scattering, may be appropriate. Additionally, detection in a microwave range may be useful in some instances and, therefore, microwave absorption techniques may be used. Still further, devices may use UV absorption detection, or RAMAN based spectrometers may be used. It is known that fourier transform mathematics are useful not only in IR detection and RAMAN spectrometers, but in other areas such as NMR spectroscopy, and is the basis for scattering techniques such as X-Ray Diffraction (XRD), Small Angle X-Ray Scattering (SAXS), and Small Angle Light Scattering (SALS). Therefore, any of these techniques or others may be appropriate dependent on the materials being detected.

Figure 6A:
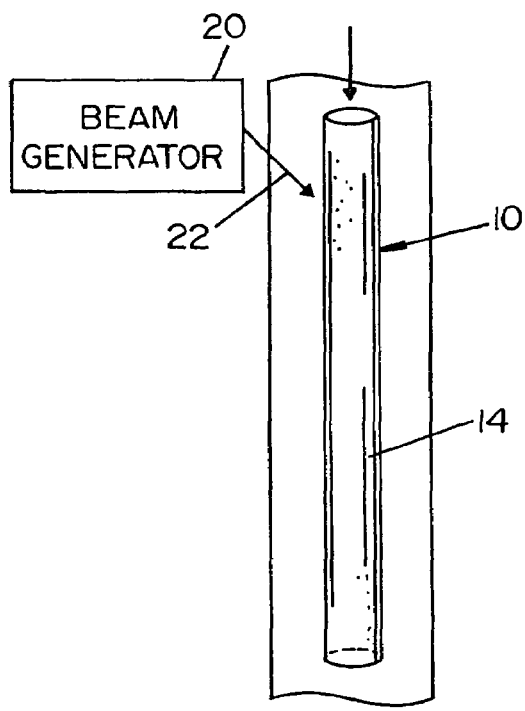
Figure 6B:
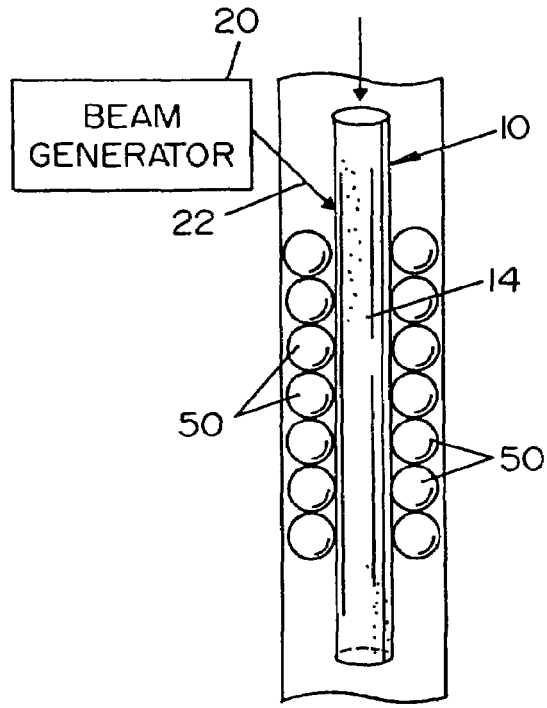

With continuing attention to the embodiments of FIG. 3 (wherein the process is undertaken in real-time), and further attention to FIGS. 6A and 6B the benefits of stabilizing transportation of the wire during the manufacturing process is illustrated. More particularly, as shown in FIG. 6A, movement of the wire, such as by twisting, wiggling or other motion, may cause the wire to move out of position such that beam 22 generated by beam generator 20 does not impinge on an intended surface location of oiled wire (10, 14). Therefore, as shown in FIG. 6B, oiled wire (10, 14) is transported, at least in this location of the manufacturing process, in a manner to reduce movement of the wire. In one embodiment, this is accomplished by providing stabilizers 50 whereby oiled wire (10, 14) is maintained in a predetermined position, within acceptable tolerances. By this design, beam 22 is able to impinge on oiled wire (10, 14) within a designated area of the wire surface. In one embodiment, stabilizers 50 may be in the form of ball bearings or other component which controls the movement of the wire.

While the foregoing has described embodiments of the present application and illustrated those embodiments described herein, it will be appreciated that other embodiments can be made and that changes can be made in the described embodiments without departing from the principles described therein. Accordingly, it is to be distinctly understood that the foregoing descriptive matter is to be interpreted merely as illustrative of the presented concepts and not as limitations thereto.

The invention claimed is:

1. A system for analyzing and controlling application of a lubricant onto a surface of a welding wire during the process of manufacturing the wire, comprising:
   an applicator positioned to receive a moving wire and to apply controlled amounts of lubricant to the wire as the welding wire passes through the applicator;
   a beam generator positioned to emit a beam which impinges onto a surface of the welding wire after the lubricant has been applied to the surface of the welding wire by the applicator;
   a detector positioned to receive a reflected beam from the surface of the welding wire, the reflected beam being generated from the impinging beam, and the reflected beam having attributes detected by the detector which determines characteristics of the lubricant on the surface of the welding wire; and
   a feedback circuit in operable connection with the detector and the applicator, wherein outputs from the detector are provided to the feedback circuit which generates feedback control signals supplied to the applicator and based on the feedback control signals, operation of the applicator is adjusted.

2. The system according to claim 1, wherein the detection of the lubricant on the surface of the welding wire is performed in real-time.

3. The system according to claim 1, wherein the beam generator and the detector are formed as a Fourier Transform Infrared system.

4. The system according to claim 1, wherein the detector collects information multiple times per second.

5. The system according to claim 1, wherein the welding wire is moving in the manufacturing process at approximately 1000 ft/min or greater.

6. The system according to claim 1, further including a welding wire transport system for moving the welding wire during the manufacturing process, wherein the welding wire transport system includes a stabilizer section.

7. The system of claim 1 wherein,
   the beam generator is part of a spectroscopic device; and
   the detector is part of the spectroscopic device.

8. An analysis system for analyzing a lubricant on a surface of a welding wire comprising:
   a beam generator configured to emit a beam with a known energy level which impinges on a surface of the welding wire as the welding wire is moved; and,
   a detector configured to detect a reflected beam from the surface of the wire, the reflected beam being generated from the impinging beam, and the reflected beam having data which permits determination of characteristics of the lubricant on the surface of the welding wire.

9. The system according to claim 8, wherein the detector measures an amount of energy absorbed by the substance on the surface of the welding wire.

10. The system according to claim 8, wherein the detection of substance on the surface of the welding wire is performed in real-time.

11. The system according to claim 8, wherein the beam generator and detector are formed as a Fourier Transform Infrared spectrometer.

12. The system according to claim 8, wherein the detector collects information multiple times per second.

13. The system according to claim 8, wherein the welding wire is moving in the manufacturing process at approximately 1000 ft/min. or greater.

14. The system according to claim 8, further including a feedback circuit in operative connection with the detector and an applicator, wherein the feedback circuit is configured to receive signals from the detector and to transmit signals to the applicator.

15. The system according to claim 8, wherein the beam generator and detector are formed as a portable hand-held unit.

16. A method for measuring an amount of a substance on a surface of a wire comprising:
   positioning at least a section of the wire and a beam generating device in a predetermined positional relationship to each other;
   generating a high-energy beam from the beam generating device at a location so the high-energy beam impinges on the section of wire;
   reflecting the high-energy beam from the section of wire as a reflected beam;
   positioning a detector at a location to receive the reflected beam;
   detecting the reflected beam by the detector; and
   determining characteristics of the substance on the surface of the wire based on the reflected beam detected by the detector.

17. The method according to claim 16, wherein the detection of the substance on the surface of the welding wire is performed in real-time.

18. The method according to claim 16, wherein the beam generator and detector are formed as a Fourier Transform Infrared system.

19. The system according to claim 16, wherein the detector collects information multiple times per second.

20. The system according to claim 16, wherein the wire is moving in the manufacturing process at approximately 1000 ft/min or greater.

* * * * *